United States Patent
Boday et al.

(10) Patent No.: US 9,549,996 B2
(45) Date of Patent: Jan. 24, 2017

(54) MATRIX INCORPORATED FLUORESCENT POROUS AND NON-POROUS SILICA PARTICLES FOR MEDICAL IMAGING

(71) Applicant: International Business Machines Corporation, Armonk, NY (US)

(72) Inventors: Dylan J. Boday, Tucson, AZ (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/703,955

(22) Filed: May 5, 2015

(65) Prior Publication Data
US 2015/0231280 A1    Aug. 20, 2015

Related U.S. Application Data

(62) Division of application No. 13/803,300, filed on Mar. 14, 2013, now Pat. No. 9,119,875.

(51) Int. Cl.
*A61K 49/00* (2006.01)
*A61K 47/48* (2006.01)
*A61K 49/18* (2006.01)

(52) U.S. Cl.
CPC ..... *A61K 49/0021* (2013.01); *A61K 47/48861* (2013.01); *A61K 49/0093* (2013.01); *A61K 49/0054* (2013.01); *A61K 49/1848* (2013.01)

(58) Field of Classification Search
CPC ............ A61K 49/1848; A61K 49/0093; A61K 9/5115; A61K 9/5192; A61K 47/48861; A61K 47/48884; A61K 49/0021; A61K 49/0065; A61K 49/1818; B82Y 5/00; C09B 67/0005; G01N 33/587
See application file for complete search history.

(56) References Cited

U.S. PATENT DOCUMENTS

| | | |
|---|---|---|
| 7,777,176 B2 | 8/2010 | Loy et al. |
| 7,923,030 B2 | 4/2011 | Lapidot et al. |
| 8,239,007 B2 | 8/2012 | Voegele et al. |
| 8,735,852 B2 | 5/2014 | Boday et al. |
| 2005/0008858 A1 | 1/2005 | Wakefield et al. |
| 2008/0020051 A1 | 1/2008 | Dahne et al. |
| 2008/0102036 A1 | 5/2008 | Poss et al. |
| 2009/0252811 A1 | 10/2009 | Lin et al. |
| 2009/0311332 A1 | 12/2009 | DeShong et al. |
| 2010/0003204 A1 | 1/2010 | Loy et al. |
| 2010/0035365 A1 | 2/2010 | Wiesner et al. |
| 2010/0038526 A1* | 2/2010 | Loy .................. C09K 11/06 250/226 |
| 2010/0172999 A1 | 7/2010 | Marteaux et al. |
| 2010/0255103 A1* | 10/2010 | Liong ............... A61K 9/5094 424/489 |
| 2010/0303716 A1 | 12/2010 | Jin et al. |
| 2011/0028662 A1* | 2/2011 | Wiesner ............ A61K 49/0032 525/478 |
| 2011/0039983 A1* | 2/2011 | Kuehner ............... B82Y 30/00 523/466 |
| 2011/0171097 A1 | 7/2011 | Chung et al. |
| 2011/0262356 A1 | 10/2011 | Bonacchi et al. |
| 2011/0268791 A1 | 11/2011 | Liu et al. |
| 2012/0021023 A1 | 1/2012 | Bekemeier et al. |
| 2013/0039858 A1* | 2/2013 | Brown ............. G01N 33/54346 424/9.3 |
| 2013/0341528 A1 | 12/2013 | Boday et al. |
| 2014/0271481 A1 | 9/2014 | Boday et al. |
| 2014/0271894 A1 | 9/2014 | Boday et al. |

FOREIGN PATENT DOCUMENTS

| | | |
|---|---|---|
| EP | 1729745 B1 | 6/2012 |
| WO | 2009038659 A2 | 3/2009 |
| WO | 2009040843 A2 | 4/2009 |
| WO | 2009140266 A2 | 11/2009 |
| WO | 2010019125 A1 | 2/2010 |

(Continued)

OTHER PUBLICATIONS

"HST hybrid silica technologies", 2 pages, http://www.hybridsilica.com/ (accessed Oct. 11, 2012).
Sokolov et al., "Novel Fluorescent Silica Nanoparticles: Towards Ultrabright Silica Nanoparticles", 16 pages, http://people.clarkson.edu/~isokolov/manuscriptSmall2008.pdf (accessed Oct. 11, 2012).
U.S. Appl. No. 13/803,604, to Boday et al., entitled "Matrix-Incorporated Fluorescent Porous Silica Particles for Drug Delivery", filed Mar. 14, 2013, assigned to International Business Machines Corporation.

(Continued)

*Primary Examiner* — Mark V Stevens
(74) *Attorney, Agent, or Firm* — Matthew J. Bussan

(57) ABSTRACT

A silica particle for medical imaging includes a bridged silane fluorescent dye incorporated throughout the particle matrix. Copolymerization of a bridged silane fluorescent dye (e.g., $(R'O)_3Si$—R—$Si(OR')_3$, where R is a fluorescent organic bridging group, and where R' is a methyl or ethyl group) and a tetralkoxysilane (e.g., $Si(OR')_4$, where R' is a methyl or ethyl group) generates particles of a predetermined size and shape. This leaves the surface of each particle available for further modification to facilitate dispersion of the particle into different media. Hence, a surface modifier may be subsequently bonded onto the particle surface. In some embodiments, poly(ethylene glycol) is selected as the surface modifier to increase dispersion of the silica particle in an aqueous media. In some embodiments, the particle is porous allowing for an additional functionality (e.g., a secondary imaging material, such as magnetic nanoparticles, and/or a pharmaceutical drug) to be loaded within the pores.

7 Claims, 5 Drawing Sheets

(56) References Cited

FOREIGN PATENT DOCUMENTS

| WO | 2011109216 A2 | | 9/2011 | |
|---|---|---|---|---|
| WO | WO 2011109216 A2 | * | 9/2011 | ....... G01N 33/54346 |
| WO | 2012018290 A1 | | 2/2012 | |
| WO | 2012021922 A1 | | 2/2012 | |
| WO | 2012109755 A1 | | 8/2012 | |

OTHER PUBLICATIONS

Matsumura et al., "A New Concept for Macromolecular Therapeutics in Cancer Chemotherapy: Mechanism of Tumoritropic Accumulation of Proteins and the Antitumor Agent Smancs", Cancer Research, 1986, vol. 46, pp. 6387-6392.

Wikipedia contributors, "Liposome", Wikipedia, The Free Encyclopedia, http://en.wikipedia.org/w/index.php?title=Liposome&oldid=532901500 (accessed Jan. 15, 2013).

Wikipedia contributors, "Mobil Composition of Matter", Wikipedia, The Free Encyclopedia, http://en.wikipedia.org/w/index.php?title=Mobil_Composition_of_Matter&oldid=480976911 (accessed Jan. 16, 2013).

Lai et al., "A Mesoporous Silica Nanosphere-Based Carrier System with Chemically Removable CdS Nanoparticle Caps for Stimuli-Responsive Controlled Release of Neurotransmitters and Drug Molecules", J. Am. Chem. Soc., 2003, vol. 125, pp. 4451-4459.

Ben N. G. Giepmans et al.; "The Fluorescent Toolbox for Assessing Protein Location and Function," 2006; AAAS; Science, vol. 312, pp. 217-224.

Lin et al., "Well-Ordered Mesoporous Silica Nanoparticles as Cell Markers", American Chemical Society, Chemistry of Materials, 2005, vol. 17, No. 18, pp. 4570-4573.

Singh et al., "Bioresponsive Mesoporous Silica Nanoparticles for Triggered Drug Release", American Chemical Society, Journal of the American Chemical Society, 2011, vol. 133, pp. 19582-19585.

Carolina de las Heras Alarcon et al., "Stimuli responsive polymers for biomedical applications," 2005, Chemical Society Reviews, vol. 34, pp. 276-285.

U.S. Appl. No. 13/803,300, to Boday et al., entitled "Matrix-Incorporated Fluorescent Porous and Non-Porous Silica Particles for Medical Imaging", filed Mar. 14, 2013, assigned to International Business Machines Corporation.

Singh et al., Supporting Information for "Bioresponsive Mesoporous Silica Nanoparticles for Triggered Drug Release", 2011, American Chemical Society, Journal of the American Chemical Society, vol. 133, pp. 19582-19585; downloaded from <http://pubs.acs.org/doi/suppl/10.1021/ja206998x/suppl_file/ja206998x_si_001.pdf> on May 19, 2015, pp. S1-S12.

Wang et al., "One-pot preparation of thermoresponsive silica-poly(N-isopropylacrylamide) nanocomposite particles in supercritical carbon dioxide," 2010, Elsevier, Journal of Colloid and Interface Science, vol. 343, pp. 141-148.

Lim et al., "Synthesis and Characterization of a Reactive Vinyl-Functionalized MCM-41: Probing the Internal Pore Structure by a Bromination Reaction," 1997, ACS, Journal of the American Chemical Society, vol. 119, No. 17, pp. 4090-4091.

Slowing et al., "Effect of Surface Functionalization of MCM-41-Type Mesoporous Silica Nanoparticles on Endocytosis by Human Cancer Cells," 2006, ACS, Journal of the American Chemical Society, vol. 128, No. 46, pp. 14792-14793.

* cited by examiner

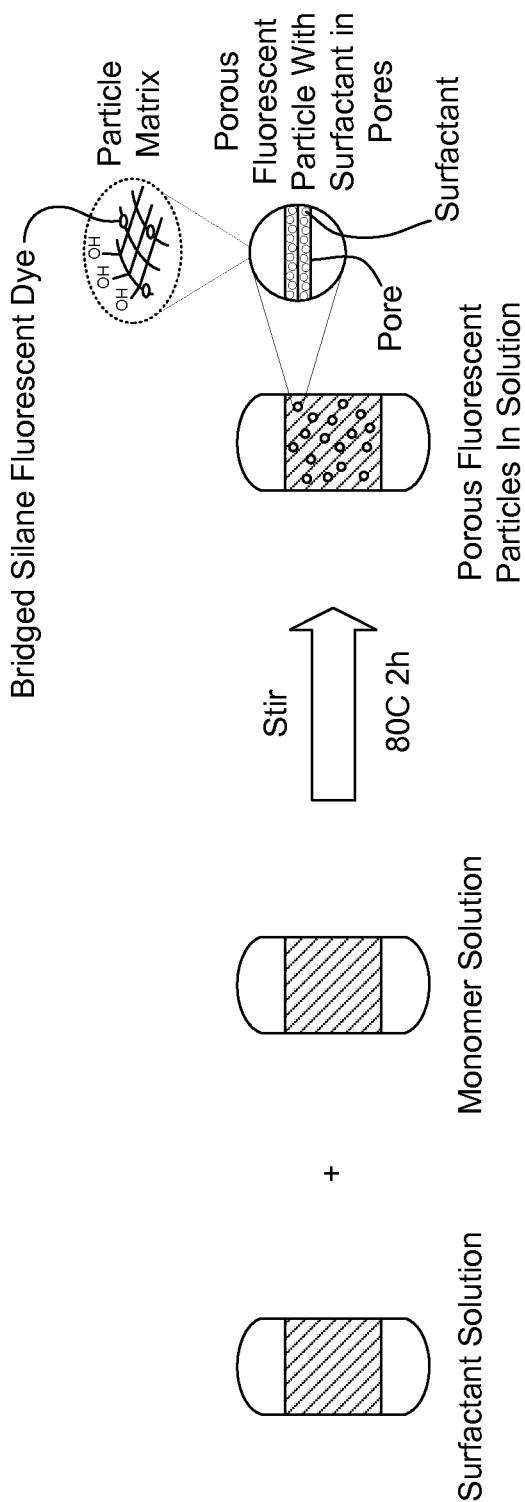
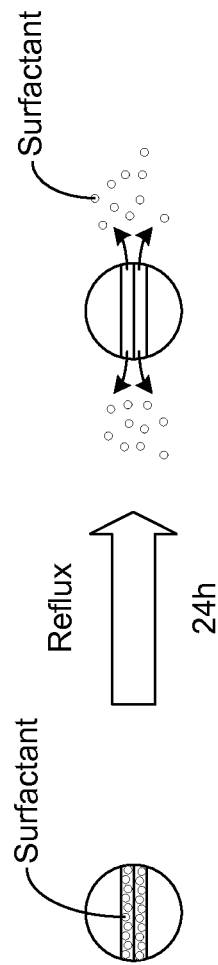
FIG. 4A
FIG. 4B

MATRIX INCORPORATED FLUORESCENT POROUS AND NON-POROUS SILICA PARTICLES FOR MEDICAL IMAGING

CROSS-REFERENCE TO RELATED APPLICATION

This patent application is a divisional application of pending U.S. patent application Ser. No. 13/803,300, filed Mar. 14, 2013, entitled "MATRIX-INCORPORATED FLUORESCENT POROUS AND NON-POROUS SILICA PARTICLES FOR MEDICAL IMAGING", which is hereby incorporated herein by reference in its entirety.

BACKGROUND OF THE INVENTION

1. Field of Invention

The present invention relates in general to the field of medical imaging. More particularly, the present invention relates to matrix-incorporated fluorescent porous and non-porous silica particles for medical imaging, and preparation methods thereof.

2. Background Art

Fluorescent nanoparticles are becoming increasingly attractive in the medical field as medical imaging aids for use in vivo and in vitro. Typically, fluorescent nanoparticles are prepared using one of two approaches: core-shell encapsulation or particle surface modification. Unfortunately, these approaches each suffer one or more of the following limitations: unintended fluorescent dye leach out; inadequate dispersion of the fluorescent nanoparticle in aqueous media; and inability of the fluorescent nanoparticle to accommodate additional functionalities (i.e., one or more functionalities beyond the fluorescent dye).

SUMMARY OF THE INVENTION

According to some embodiments of the present invention, a silica particle for medical imaging includes a bridged silane fluorescent dye incorporated throughout the particle matrix. Copolymerization of a bridged silane fluorescent dye (e.g., $(R'O)_3Si-R-Si(OR')_3$, where R is a fluorescent organic bridging group, and where R' is a methyl or ethyl group) and a tetralkoxysilane (e.g., $Si(OR')_4$, where R' is a methyl or ethyl group) generates particles of a predetermined size and shape. This leaves the surface of each particle available for further modification to facilitate dispersion of the particle into different media. Hence, a surface modifier may be subsequently bonded onto the particle surface. In some embodiments, poly(ethylene glycol) is selected as the surface modifier to increase dispersion of the silica particle in an aqueous media. In some embodiments, the particle is porous allowing for an additional functionality (e.g., a secondary imaging material, such as magnetic nanoparticles, and/or a pharmaceutical drug or other payload) to be loaded within the pores. In some embodiments, the resulting particles are administered to a specimen and analyzed through the use of a fluorescence microscope or other fluorescence inducing instruments.

BRIEF DESCRIPTION OF THE DRAWINGS

The preferred exemplary embodiments of the present invention will hereinafter be described in conjunction with the appended drawings, where like designations denote like elements.

FIGS. 4A-4D depict respective stages in a prophetic example of a method for producing matrix-incorporated fluorescent porous silica particles in accordance with some embodiments of the present invention.

DETAILED DESCRIPTION OF THE PREFERRED EMBODIMENTS

1. Overview

Figure 1:
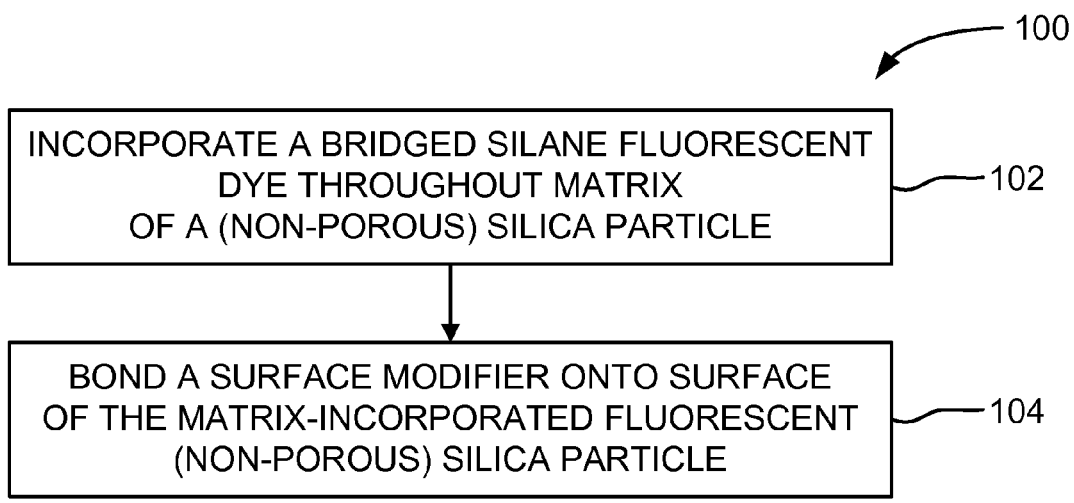
FIG. 1 is a flow diagram of a method for producing a matrix-incorporated fluorescent (non-porous) silica particle in accordance with some embodiments of the present invention.

In accordance with some embodiments of the present invention, a silica particle for medical imaging includes a bridged silane fluorescent dye incorporated throughout the particle matrix. Copolymerization of a bridged silane fluorescent dye (e.g., $(R'O)_3Si-R-Si(OR')_3$, where R is a fluorescent organic bridging group, and where R' is a methyl or ethyl group) and a tetralkoxysilane (e.g., $Si(OR')_4$, where R' is a methyl or ethyl group) generates particles of a predetermined size and shape. This leaves the surface of each particle available for further modification to facilitate dispersion of the particle into different media. Hence, a surface modifier may be subsequently bonded onto the particle surface. In some embodiments, poly(ethylene glycol) is selected as the surface modifier to increase dispersion of the silica particle in an aqueous media. In some embodiments, the particle is porous allowing for an additional functionality (e.g., a secondary imaging material, such as magnetic nanoparticles, and/or a pharmaceutical drug or other payload) to be loaded within the pores. In some embodiments, the resulting particles are administered to a specimen and analyzed through the use of a fluorescence microscope or other fluorescence inducing instruments.

2. Detailed Description

An organic fluorescent dye is incorporated throughout the matrix of a porous or non-porous silica particle in accordance with some embodiments of the present invention. Incorporation of an organic fluorescent dye throughout a particle's matrix is highly advantageous over prior art approaches, such as incorporating an organic fluorescent dye onto the surface of a particle via surface modification or entrapping an organic fluorescent dye within a particle via core-shell encapsulation. For example, a matrix-incorporated fluorescent porous or non-porous silica particle in accordance with some embodiments of the present invention can be surface modified to have aqueous dispersive properties. Moreover, a matrix-incorporated fluorescent porous or non-porous silica particle in accordance with some embodiments of the present invention has zero dye leach out.

Matrix-incorporated fluorescent porous and non-porous silica particles in accordance with some embodiments of the present invention can be produced in various shapes (e.g., spheres, rods, discoids, gyroids, etc.) and in a wide range of sizes from nano to micro diameters. Such particles can be produced, for example, in homogeneous sizes.

In accordance with some embodiments of the present invention, an organic bridged fluorescent silane dye is incorporated into the silica matrix of the particle to prevent leach out. Bridged silane fluorescent dyes are bridged silane monomers with the general chemical structure of $(R'O)_3Si$—R—$Si(OR')_3$, where the R bridging group is a fluorescent organic group and where R' is a methyl or ethyl group. Copolymerization of the bridged silane fluorescent dye and a tetralkoxysilane (e.g., $Si(OR')_4$, where R' is a methyl or ethyl group) in the presence of a surfactant generates the matrix-incorporated fluorescent porous silica particles. Bridged silane fluorescent dyes are distributed by reaction kinetics throughout the silica matrix and, hence, bridged silane fluorescent dyes become matrix-incorporated via the copolymerization. Ordinary (i.e., non-bridged) fluorescent silane dyes, on the other hand, only surface modify the porous or non-porous silica particle due to reaction kinetics. Zero dye leach out is achieved because the bridged silane fluorescent dye is matrix-incorporated into the silica matrix of the particle, and each bridged fluorescent dye molecule is matrix-incorporated with up to six points of attachment.

Organic bridged fluorescent silane dyes can be tailored to produce different emissions (typically, in either the visual spectrum or the near-infrared (NIR) spectrum) depending on which fluorescent organic group is selected as the bridging group. For example, in accordance with some embodiments of the present invention the organic bridged fluorescent silane dye is tailored to produce emissions suitable for a particular method of viewing. This tailoring is accomplished by selecting, as the bridging group of the organic bridged fluorescent silane dye, a fluorescent organic group that fluorescences within a range of wavelengths suitable for a particular method of viewing. Fluorescence can be visualized using fluorescence microscopy, UV black light (visual spectrum), night vision goggles (NIR), or other methods chosen by those skilled in the art.

The use of a matrix-incorporated fluorescent porous or non-porous silica particle for use in medical imaging, where a fluorescent dye is bound within the matrix of the silica particle and where the silica particle is surface modified in accordance with some embodiments of the present invention, is highly advantageous over prior art approaches, such as core-shell encapsulation or particle surface modification. These prior art approaches are limited by fluorescent dye leach out and cannot accommodate additional surface modification because the surface functionalities of the particle are already taken up by a dye molecule. In contrast to these prior art approaches, there is no dye leach out from a matrix-incorporated fluorescent porous or non-porous silica particle in accordance with some embodiments of the present invention because the fluorescent dye is bound within the matrix of the silica particle. Also in contrast to these prior art approaches, because the surface functionalities are not already taken up by a dye molecule, the surface of a matrix-incorporated fluorescent porous or non-porous silica particle in accordance with some embodiments of the present invention is available for additional surface modification to allow the particles to be dispersed in different systems.

Hence, after creation of matrix-incorporated fluorescent silica particles, be they porous or nonporous, the surface of the particles can be modified in accordance with some embodiments of the present invention to allow the particles to be disbursed in different media. One example of a surface modification would be the use of a poly(ethylene glycol) silane. Other surface modifiers may also be chosen by those skilled in the art.

In accordance with some embodiments of the present invention, copolymerization of a fluorescent bridged bis/tris alkoxysilane with a tetralkoxysilane generates fluorescent porous or non-porous silica particles of a predetermined shape and size. The copolymerization incorporates a fluorescent dye directly into the matrix of the silica particle thereby preventing dye leach out. The copolymerization reaction also leaves the surface of each particle available for subsequent modification to disperse into different media. Hence, the particles may be tailored, through surface modification, to disperse into a particular media. Because the particles are porous in some embodiments, an additional functionality can be added within the pores for subsequent release. The resulting particles can then be administered to a specimen and analyzed through the use of a fluorescence microscope or other fluorescence inducing instruments.

The pores of a matrix-incorporated fluorescent porous silica particle in accordance with some embodiments of the present invention are available to accommodate additional functionalities (i.e., one or more functionalities beyond the fluorescent dye). For example, the pores may carry a secondary imaging material, such as magnetic nanoparticles, and/or a pharmaceutical drug molecule or other payload. As used herein, including the claims, the term "payload" includes molecules of various sizes, shapes and functionalities including pharmaceutical drug molecules, neurotransmitters, biocides, genes, and proteins.

A matrix-incorporated fluorescent porous silica particle in accordance with some embodiments of the present invention may be, for example, a MCM-41 type (i.e., Mobil Composition of Matter No. 41) or MCM-48 type (i.e., Mobil Composition of Matter No. 48) mesoporous silica nanoparticle (MSN). The acronym "MCM" is also referred to in the art as "Mobil Crystalline Material". MCM-type mesoporous silica materials typically possess several desirable features (e.g., stable mesoporous structures, large surface areas, tunable pore diameters and volumes, and well-defined surface properties) that make these materials ideal for hosting molecules of various sizes, shapes, and functionalities. Another advantage of MSNs is that they may be organically functionalized. Hence, in accordance with some embodiments of the present invention, the matrix-incorporated fluorescent porous silica particle may be a MSN. Matrix-incorporated fluorescent porous silica particles, including MSNs, can be generated in accordance with some embodiments of the present invention with homogenous size distribution, various shapes, and a wide spectrum of fluorescent emissions.

One skilled in the art will appreciate, however, that a matrix-incorporated fluorescent porous silica particle in accordance with some embodiments of the present invention is not limited to MSNs or MCM-type mesoporous silica materials.

FIG. 1 is a flow diagram of a method 100 for producing a matrix-incorporated fluorescent (non-porous) silica particle in accordance with some embodiments of the present invention. The method 100 sets forth the preferred order of the steps. It must be understood, however, that the various steps may occur at any time relative to one another.

The method 100 begins by incorporating a bridged silane fluorescent dye throughout a matrix of a silica particle (step 102). In accordance with some embodiments of the present invention, step 102 is performed via a copolymerization reaction between a bridged silane fluorescent dye and a tetralkoxysilane. For example, a matrix-incorporated fluorescent silica particle in accordance with some embodiments of the present invention may be manufactured using a modified Stöber process to incorporate a bridged silane fluorescent dye into the matrix of the silica material. The Stöber process, itself, and modifications thereof are well known in the art. A modified Stöber process, for example, disclosed in U.S. Pat. No. 7,777,176 B2, issued to Loy et al. on Aug. 17, 2010, entitled "COMPOSITION AND METHOD TO CHARACTERIZE MEMBRANES' DEFECTS", which is hereby incorporated herein by reference in its entirety.

In accordance with some embodiments of the present invention, the Stöber process is modified to introduce a bridged silane fluorescent dye into the copolymerization reaction to incorporate the bridged silane fluorescent dye throughout the matrix of the resultant silica particles. In accordance with some embodiments of the present invention, the bridged silane fluorescent dye has the general chemical structure (R'O)$_3$Si—R—Si(OR')$_3$, wherein R is a fluorescent organic bridging group, and wherein R' is a methyl or ethyl group. Bridged silane fluorescent dyes may be readily synthesized using processes well known in the art. For example, the synthesis of a myriad of bridged silane fluorescent dyes is disclosed in U.S. Pat. No. 7,777,176 B2, incorporated by reference above.

The bridged silane fluorescent dye can be added throughout the silica matrix through copolymerization of a tetralkoxysilane and a bridged silane fluorescent dye using a modified Stöber process. The tetralkoxysilane in step 102 may be, for example, tetraethyl orthosilicate (TEOS) or any other suitable tetralkoxysilane (e.g., Si(OR')$_4$, where R' is a methyl or ethyl group).

In accordance with some embodiments of the present invention, the matrix-incorporated fluorescent silica particle is a nanoparticle approximately 15 to 1000 nm in diameter.

One example of a bridged silane fluorescent dye that could be used in step 102 is 4,4'-bis(4-(triethoxysilyl)styryl) biphenyl, which can easily be incorporated into the Stöber process. Other bridged silane fluorescent dyes both in the visual spectrum and near-infrared (NIR) spectrum may be also chosen by those skilled in the art. Suitable fluorescent dyes include, but are not limited to, monomers with the general chemical structure of (R'O)$_3$Si—R—Si(OR')$_3$, where the R bridging group is a fluorescent organic group and where R' is a methyl or ethyl group. The amount of bridged silane fluorescent dye can be varied but generally less than 1.0 mol % is acceptable. Particle size can be controlled using chemical concentration. For example, in the modified Stöber process, the concentration of water can be used to vary particle size.

The method 100 continues by bonding a surface modifier onto a surface of the matrix-incorporated fluorescent silica particles (step 104). The surface of the matrix-incorporated fluorescent silica particle is modified to allow the particles to be disbursed in different media. For example, the surface of the particles can be additionally modified using a poly(ethylene glycol) (PEG) silane to allow the particles to be disbursed in an aqueous media. Other surface modifiers may be chosen by those skilled in the art.

Surface modification of the particles with PEG may make the matrix-incorporated fluorescent silica particle non-toxic for in vivo.

Surface modification of the particles with PEG may also serve to increase the Enhanced Permeability and Retention (EPR) effect. Typically, PEG surface modification of silica nanoparticles increases the EPR effect. The EPR effect is the property by which certain sizes of molecules (typically liposomes, nanoparticles, and macromolecular drugs) tend to accumulate in tumor tissue much more than those same molecules tend to accumulate in normal tissue. Matrix-incorporated fluorescent silica particles in accordance with some embodiments of the present invention may be tailored in size to be site-selective. Moreover, this site-selectivity may be enhanced via surface modification of the particles with PEG.

Figure 2A:
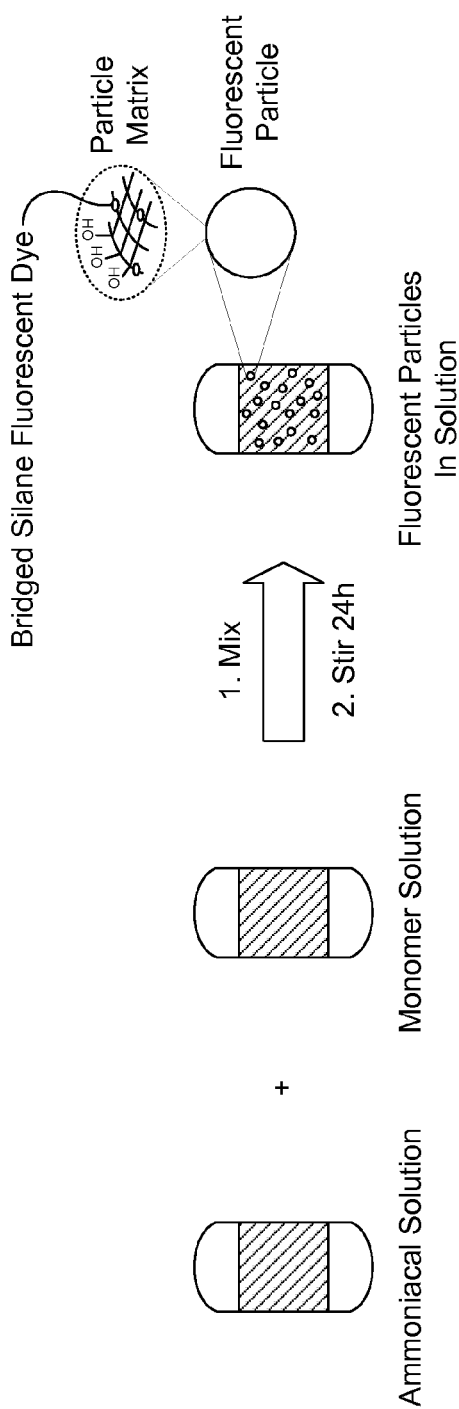
FIGS. 2A-2B depict respective stages in a prophetic example of a method for producing matrix-incorporated fluorescent (non-porous) silica particles in accordance with some embodiments of the present invention.
Figure 2B:
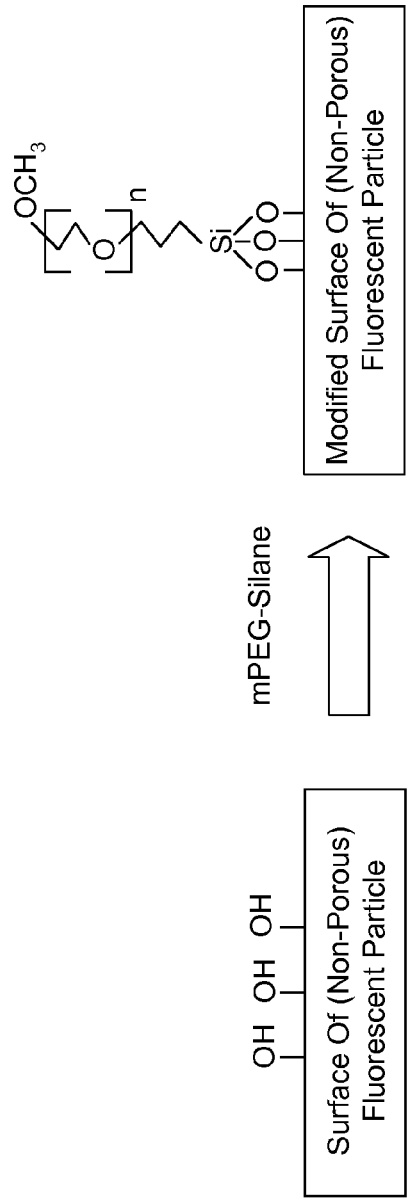

FIGS. 2A-2B depict respective stages in a prophetic example of a method for producing matrix-incorporated fluorescent (non-porous) silica particles in accordance with some embodiments of the present invention.

Preparation of Matrix-Incorporated Fluorescent (Non-Porous) Silica Nanoparticles FIG. 2A depicts a matrix-incorporated fluorescent silica nanoparticle preparation stage in a prophetic example of a method for producing matrix-incorporated fluorescent porous silica nanoparticles in accordance with some embodiments of the present invention. Particles are prepared through a modified Stöber process using ammonia, deionized water, tetraethyl orthosilicate (TEOS), ethanol, and a bridged silane fluorescent dye (i.e., in this prophetic example, 4,4'-bis(4-(triethoxysilyl)styryl)biphenyl). TEOS is commercially available from chemical suppliers, such as Sigma-Aldrich, St. Louis, Mo. An exemplary synthesis of the bridged silane fluorescent dye used in this prophetic example is described below.

To a glass vial, 2M ammonia (3.75 mL) and water (0.63 mL) are added to generate an ammoniacal solution. To a second glass vial, TEOS (0.38 mL, $1.70 \times 10^{-3}$ mol), 200 proof ethanol (5.24 mL), and the bridged silane fluorescent dye (0.01-1.0 mol %) are then added generate a monomer solution. In this prophetic example, 4,4'-bis(4-(triethoxysilyl)styryl)biphenyl (11.61 mg, $1.70 \times 10^{-5}$ mol) is used as the bridged silane fluorescent dye. Next, the ammoniacal solution is added to the monomer solution and stirred vigorously for 24 hours. Particles are then centrifuged, washed, and dried to remove any unreacted silane. Next, the particles are re-dispersed in a solvent and the surface modifier is added and stirred for a few hours. Particles are then centrifuged, washed, and dried yielding fluorescent matrix modified silica nanoparticles. The bridged silane fluorescent dye used in this prophetic example (i.e., 4,4'-bis(4-(triethoxysilyl)styryl)biphenyl) may be synthesized as discussed below.

Synthesis of Bridged Silane Fluorescent Dye

The bridged silane fluorescent dye used in this prophetic example (i.e., 4,4'-bis(4-(triethoxysilyl)styryl)biphenyl) is synthesized using (triethoxysilyl)styrene, 4,4'-dibromephenyl, anhydrous toluene, tri-o-tolylphosphine, and palladium acetate. (Triethoxysilyl)styrene, 4,4'-dibromephenyl, tri-o-tolylphosphine, and palladium acetate are commercially available from chemical suppliers, such as Sigma-Aldrich, St. Louis, Mo. To a three neck 25 mL round bottom flask, (triethoxysilyl)styrene (1.006 g, 3.8 mmol) is added. To this solution, a magnetic stir bar and 4,4'-dibromephenyl (1.176 g, 3.8 mmol) are added, followed by anhydrous toluene (10 mL). To this solution, tri-o-tolylphosphine (0.085 g, $2.6 \times 10^{-5}$ mol) along with palladium acetate (0.015 g, $4.45 \times 10^{-5}$ mol) are added. This solution is stirred and heated at 105° C. After an hour, an additional amount of (triethoxysilyl)styrene (0.9006 g, 3.4 mmol) is added along with additional anhydrous toluene (10 mL). The solution is allowed to react for 24 h. The brown solution is vacuum suctioned through CELITE® to remove palladium. The solution is removed in vacuo yielding 4,4'-bis(4-(triethoxysilyl)styryl)biphenyl, a yellow solid.

PEG Surface Modification of Matrix-Incorporated Fluorescent (Non-Porous) Silica Nanoparticles FIG. 2B depicts a PEG surface modification stage in a prophetic example of a method for producing matrix-incorporated fluorescent silica nanoparticles in accordance with some embodiments of the present invention. In order to make the matrix-incorporated fluorescent silica nanoparticles non-toxic for in vivo, the surface is additionally modified with polyethylene glycol (PEG). Dried particles (100 mg) are dispersed in a solution of methoxy-PEG-silane (3 mM) in toluene (5 mL) containing 2M Ammonia (catalyst) added dropwise until the pH 9. Particles are allowed to stir for 4 h at 60° C. Methoxy-PEG-silane is commercially available from chemical suppliers, such as Sigma-Aldrich, St. Louis, Mo. The solution is then filtered and extensively washed with toluene and ethanol, and dried in vacuo.

Figure 3:
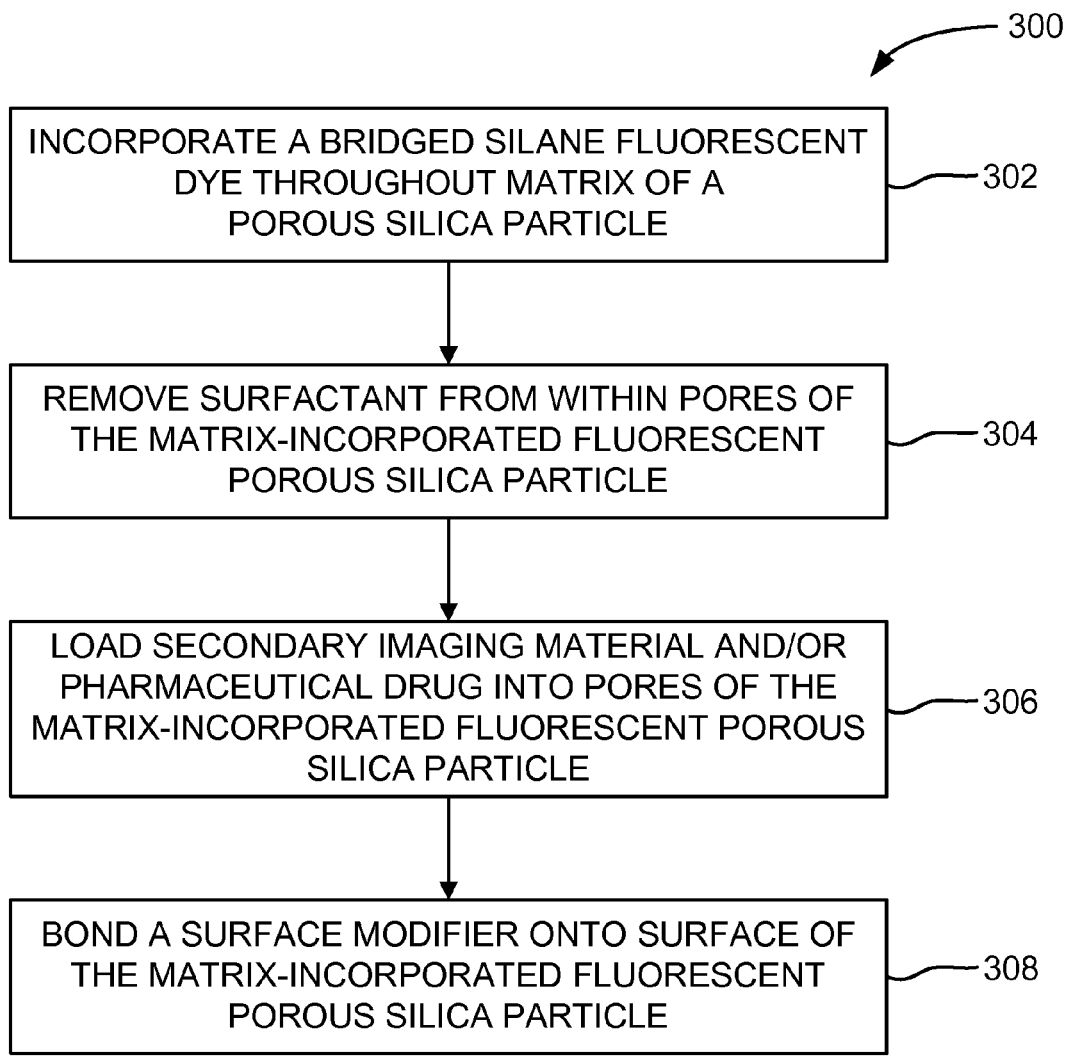
FIG. 3 is a flow diagram of a method for producing a matrix-incorporated fluorescent porous silica particle in accordance with some embodiments of the present invention.

FIG. 3 is a flow diagram of a method 300 for producing a matrix-incorporated fluorescent porous silica particle in accordance with some embodiments of the present invention. The method 300 sets forth the preferred order of the steps. It must be understood, however, that the various steps may occur at any time relative to one another.

The method 300 begins by incorporating a bridged silane fluorescent dye throughout a matrix of a porous silica particle (step 302). In accordance with some embodiments of the present invention, step 302 is performed via a copolymerization reaction between a bridged silane fluorescent dye and a tetralkoxysilane in the presence of a surfactant. For example, a matrix-incorporated fluorescent porous silica particle in accordance with some embodiments of the present invention may be manufactured using a modified Lai et al. synthesis to incorporate a bridged silane fluorescent dye into the matrix of the silica material. The Lai et al. synthesis, itself, is well known in the art. The Lai et al. synthesis is, for example, disclosed in Lai et al., "A Mesoporous Silica Nanosphere-Based Carrier System with Chemically Removable CdS Nanoparticle Caps for Stimuli-Responsive Controlled Release of Neurotransmitters and Drug Molecules", J. Am. Chem. Soc. 2003, Vol. 125, Pages 4451-4459, which is hereby incorporated herein by reference in its entirety.

In accordance with some embodiments of the present invention, the Lai et al. synthesis is modified to introduce a bridged silane fluorescent dye into the copolymerization reaction to incorporate the bridged silane fluorescent dye throughout the matrix of the resultant porous silica particles. In accordance with some embodiments of the present invention, the bridged silane fluorescent dye has the general chemical structure $(R'O)_3Si-R-Si(OR')_3$, wherein R is a fluorescent organic bridging group, and wherein R' is a methyl or ethyl group. Bridged silane fluorescent dyes may be readily synthesized using processes well known in the art. For example, the synthesis of a myriad of bridged silane fluorescent dyes is disclosed in U.S. Pat. No. 7,777,176 B2, incorporated by reference above.

The bridged silane fluorescent dye can be added throughout the silica matrix through copolymerization of a tetralkoxysilane and a bridged silane fluorescent dye in the presence of a surfactant. The tetralkoxysilane in step 302 may be, for example, tetraethyl orthosilicate (TEOS) or any other suitable tetralkoxysilane (e.g., $Si(OR')_4$, where R' is a methyl or ethyl group).

The surfactant in step 302 may be, for example, cetyltrimethylammonium bromide (CTAB) or any other suitable surfactant. The surfactant is referred to as a "template surfactant" because it serves as a template for the pores of the porous matrix-incorporated fluorescent silica nanoparticles. That is, the pore diameter can be controlled by employing surfactants with different chain lengths. In accordance with some embodiments of the present invention, the matrix-incorporated fluorescent porous silica particle is a nanoparticle or microparticle approximately 100 to 2000 nm in diameter, and the pores of the silica particle have an average diameter of approximately 1.5 to 20 nm.

One example of a bridged silane fluorescent dye that could be used in step 302 is 4,4'-bis(4-(triethoxysilyl)styryl)biphenyl, which can easily be incorporated into the Lai et al. synthesis. Other bridged silane fluorescent dyes both in the visual spectrum and near-infrared (NIR) spectrum may be also chosen by those skilled in the art. Suitable fluorescent dyes include, but are not limited to, monomers with the general chemical structure of $(R'O)_3Si-R-Si(OR')_3$, where the R bridging group is a fluorescent organic group and where R' is a methyl or ethyl group. The amount of bridged silane fluorescent dye can be varied but generally less than 1.0 mol % is acceptable. Particle size can be controlled by stir speed.

The method 300 continues by removing the surfactant within pores of the porous silica particle (step 304). In step 304 the surfactant is removed to allow the pores to be filled with a secondary imaging material, such as magnetic nanoparticles, and/or a pharmaceutical drug or other payload. For example, the surfactant (e.g., CTAB) is removed in step 104 to open the pores for accepting a secondary imaging material, such as magnetic nanoparticles, and/or a pharmaceutical drug or other payload.

The method 300 continues by loading a secondary imaging material within of the pores of the porous silica particle (step 306). In accordance with some embodiments of the present invention, step 306 is performed by loading a secondary imaging material, such as magnetic nanoparticles, into the pores of the matrix-incorporated fluorescent porous silica particle. As an example, magnetic nanoparticles can be integrated into the pores in step 306. The magnetic nanoparticles may be, for example, $Fe_3O_4$ (also referred to as "magnetite") nanoparticles, cobalt ferrite nanoparticles, or other magnetic nanoparticles known in the art. The magnetic nanoparticles, which have a diameter smaller than that of the pores, are prepared using conventional techniques known to those skilled. Other secondary imaging materials may be loaded within the pores, in lieu of, or in addition to, magnetic nanoparticles. Also, a pharmaceutical drug or other payload may be loaded within the pores in lieu of, or in addition to, a secondary imaging material. As an example, vancomycin, a drug used to treat colitis, can be integrated into the pores in step 306. Other pharmaceutical drugs or payloads may be chosen by those skilled in the art.

The method 300 continues by bonding a surface modifier onto a surface of the matrix-incorporated fluorescent porous silica particles (step 306). The surface of the matrix-incorporated fluorescent porous silica particle is modified to allow the particles to be disbursed in different media. For example, the surface of the particles can be additionally modified using a poly(ethylene glycol) (PEG) silane to allow the particles to be disbursed in an aqueous media. Other surface modifiers may be chosen by those skilled in the art.

Surface modification of the particles with PEG may make the matrix-incorporated fluorescent porous silica particle non-toxic for in vivo.

Surface modification of the particles with PEG may also serve to increase the Enhanced Permeability and Retention (EPR) effect. Typically, PEG surface modification of silica nanoparticles increases the EPR effect. The EPR effect is the property by which certain sizes of molecules (typically liposomes, nanoparticles, and macromolecular drugs) tend to accumulate in tumor tissue much more than those same molecules tend to accumulate in normal tissue. Matrix-incorporated fluorescent porous silica particles in accordance with some embodiments of the present invention may be tailored in size to be site-selective. Moreover, this site-selectivity may be enhanced via surface modification of the particles with PEG.

FIGS. 4A-4D depict respective stages in a prophetic example of a method for producing matrix-incorporated fluorescent porous silica particles in accordance with some embodiments of the present invention.

Preparation of Matrix-Incorporated Fluorescent Porous Silica Nanoparticles

FIG. 4A depicts a matrix-incorporated fluorescent porous silica nanoparticle preparation stage in a prophetic example of a method for producing matrix-incorporated fluorescent porous silica nanoparticles in accordance with some embodiments of the present invention. Particles are prepared through a modified Lai et al. synthesis using n-cetyltrimethylammonium bromide (CTAB), sodium hydroxide (NaOH), deionized water, tetraethyl orthosilicate (TEOS), and a bridged silane fluorescent dye (i.e., in this prophetic example, 4,4'-bis(4-(triethoxysilyl)styryl)biphenyl). CTAB and TEOS are commercially available from chemical suppliers, such as Sigma-Aldrich, St. Louis, Mo. An exemplary synthesis of the bridged silane fluorescent dye used in this prophetic example is described below.

CTAB (1.00 g, $2.74 \times 10^{-3}$ mol) is dissolved in deionized water (480 mL) in a 1000 mL round bottom flask with a condenser. In this prophetic example, CTAB is a template surfactant. Aqueous NaOH (2.00M, 3.50 mL) is then added to the CTAB solution, followed by raising the temperature of this surfactant solution to 80° C. using an oil bath.

TEOS (6.2 mL, $2.78 \times 10^{-2}$ mol) and the bridged silane fluorescent dye (0.01-1.0 mol %) are then added to the surfactant solution. In this prophetic example, 4,4'-bis(4-(triethoxysilyl)styryl)biphenyl (175.5 mg, $2.57 \times 10^{-4}$ mol) is used as the bridged silane fluorescent dye. The mixture is allowed to stir for 2 h to give rise to white precipitate. The solid white product is filtered, washed with deionized water and methanol, and dried in air. The bridged silane fluorescent dye used in this prophetic example (i.e., 4,4'-bis(4-(triethoxysilyl)styryl)biphenyl) may be synthesized as discussed below.

Synthesis of Bridged Silane Fluorescent Dye

The bridged silane fluorescent dye used in this prophetic example (i.e., 4,4'-bis(4-(triethoxysilyl)styryl)biphenyl) is synthesized using (triethoxysilyl)styrene, 4,4'-dibromephenyl, anhydrous toluene, tri-o-tolylphosphine, and palladium acetate. (Triethoxysilyl)styrene, 4,4'-dibromephenyl, tri-o-tolylphosphine, and palladium acetate are commercially available from chemical suppliers, such as Sigma-Aldrich, St. Louis, Mo. To a three neck 25 mL round bottom flask, (triethoxysilyl)styrene (1.006 g, 3.8 mmol) is added. To this solution, a magnetic stir bar and 4,4'-dibromephenyl (1.176 g, 3.8 mmol) are added, followed by anhydrous toluene (10 mL). To this solution, tri-o-tolylphosphine (0.085 g, $2.6 \times 10^{-5}$ mol) along with palladium acetate (0.015 g, $4.45 \times 10^{-5}$ mol) are added. This solution is stirred and heated at 105° C. After an hour, an additional amount of (triethoxysilyl)styrene (0.9006 g, 3.4 mmol) is added along with additional anhydrous toluene (10 mL). The solution is allowed to react for 24 h. The brown solution is vacuum suctioned through CELITE® to remove palladium. The solution is removed in vacuo yielding 4,4'-bis(4-(triethoxysilyl)styryl)biphenyl, a yellow solid.

Removal of Surfactant from Matrix-Incorporated Fluorescent Porous Silica Nanoparticles FIG. 4B depicts a surfactant removal stage in a prophetic example of a method for producing matrix-incorporated fluorescent porous silica nanoparticles in accordance with some embodiments of the present invention. To remove the surfactant template (CTAB), as-synthesized particles (100 mg) are refluxed for 24 h in a solution of HCL (9.00 mL, 37.4%) and methanol (160 mL), followed by extensive washes with deionized water and methanol. The resulting surfactant-removed silica nanoparticles are dried in vacuo to remove remaining solvent in the mesopores.

Figure 4C:
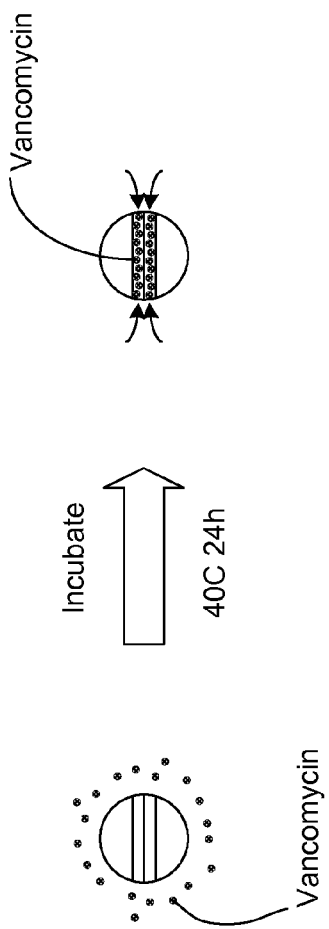

Loading Pharmaceutical Drug within Pores of Matrix-Incorporated Porous Fluorescent Silica Nanoparticles FIG. 4C depicts a secondary imaging loading stage in a prophetic example of a method for producing matrix-incorporated fluorescent porous silica nanoparticles in accordance with some embodiments of the present invention. Purified matrix-incorporated fluorescent porous silica nanoparticles (100 mg) are incubated in a PBS buffer solution (0.60 mL, pH 7.4) of vancomycin (3.00 µmol) for 24 h at 40° C. Vancomycin hydrochloride (also referred to herein as "vancomycin") is commercially available from chemical suppliers, such as Sigma-Aldrich, St. Louis, Mo. The PBS (phosphate buffered saline) buffer solution (10.00 mM, pH 7.4) may be prepared earlier with the total ionic strength of 0.06 M.

Figure 4D:
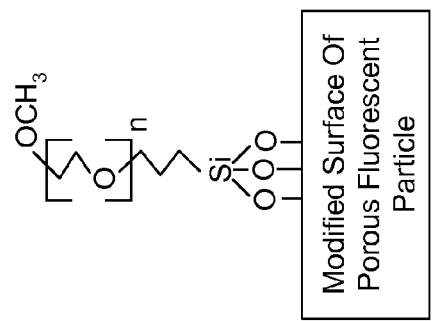
Figure 4D:

PEG Surface Modification of Matrix-Incorporated Fluorescent (Non-Porous) Silica Nanoparticles FIG. 4D depicts a PEG surface modification stage in a prophetic example of a method for producing matrix-incorporated fluorescent silica nanoparticles in accordance with some embodiments of the present invention. In order to make the matrix-incorporated fluorescent silica nanoparticles non-toxic for in vivo, the surface is additionally modified with polyethylene glycol (PEG). Dried particles (100 mg) are dispersed in a solution of methoxy-PEG-silane (3 mM) in toluene (5 mL) containing 2M Ammonia (catalyst) added dropwise until the pH 9. Particles are allowed to stir for 4 h at 60° C. Methoxy-PEG-silane is commercially available from chemical suppliers, such as Sigma-Aldrich, St. Louis, Mo. The solution is then filtered and extensively washed with toluene and ethanol, and dried in vacuo.

One skilled in the art will appreciate that many variations are possible within the scope of the present invention. Thus, while the present invention has been particularly shown and described with reference to particular embodiments thereof, it will be understood by those skilled in the art that these and other changes in form and detail may be made therein without departing from the spirit and scope of the present invention.

What is claimed is:

1. A method of synthesizing a porous silica particle for medical imaging, comprising the steps of:
   incorporating a bridged silane fluorescent dye throughout a matrix of the porous silica particle via a copolymerization reaction between a bridged silane fluorescent dye and a tetralkoxysilane in the presence of a surfactant, wherein the bridged silane fluorescent dye has the general chemical structure (R'O)3Si—R—Si(OR')3, wherein R is a fluorescent organic bridging group, and wherein R' is a methyl or ethyl group;
   removing the surfactant from within pores of the porous silica particle;
   loading an additional functionality within the pores of the porous silica particle, wherein the additional functionality comprises at least one of an imaging material or a pharmaceutical drug;
   bonding a surface modifier onto a surface of the porous silica particle, wherein the surface modifier comprises poly(ethylene glycol);
   wherein the bridged silane fluorescent dye comprises 4,4'-bis(4-(triethoxysilyl)-styryl)biphenyl.

2. The method as recited in claim 1, wherein the tetralkoxysilane comprises tetraethyl orthosilicate (TEOS).

3. The porous silica particle as recited in claim 1, wherein the porous silica particle is a nanoparticle or microparticle approximately 100 to 2000 nm in diameter, and wherein the pores of the porous silica particle have an average diameter of approximately 1.5 to 20 nm.

4. The method as recited in claim 1, wherein the additional functionality comprises a pharmaceutical drug.

5. The method as recited in claim 1, wherein the step of bonding a surface modifier onto a surface of the porous silica particle comprises dispersing the porous silica particle in a solvent and adding a silane-based surface modifier.

6. The method as recited in claim 5, wherein the solvent comprises toluene and the silane-based surface modifier comprises methoxy-poly(ethylene glycol)-silane.

7. A method of synthesizing a porous silica particle for medical imaging, comprising the steps of:
   incorporating a bridged silane fluorescent dye throughout a matrix of the porous silica particle via a copolymerization reaction between a bridged silane fluorescent dye and a tetralkoxysilane in the presence of a surfactant, wherein the bridged silane fluorescent dye comprises 4,4'-bis(4-(triethoxysilyl)styryl)biphenyl and the tetralkoxysilane comprises tetraethyl orthosilicate (TEOS);
   removing the surfactant from within pores of the porous silica particle;
   loading an additional functionality within the pores of the porous silica particle, wherein the additional functionality comprises at least one of an imaging material or a pharmaceutical drug;
   bonding a surface modifier onto a surface of the silica particle, wherein the surface modifier comprises poly(ethylene glycol).

* * * * *